United States Patent [19]
Tsuchihashi et al.

[11] Patent Number: 5,712,098
[45] Date of Patent: Jan. 27, 1998

[54] HEREDITARY HEMOCHROMATOSIS DIAGNOSTIC MARKERS AND DIAGNOSTIC METHODS

[75] Inventors: Zenta Tsuchihashi, Menlo Park; Andreas Gnirke, San Carlos; Winston J. Thomas; Dennis T. Drayna, both of San Mateo; David Ruddy, San Francisco; Roger K. Wolff, Belmont; John N. Feder, San Callos, all of Calif.

[73] Assignee: Mercator Genetics, Menlo Park, Calif.

[21] Appl. No.: 632,673

[22] Filed: Apr. 16, 1996

Related U.S. Application Data

[63] Continuation-in-part of Ser. No. 630,912, Apr. 4, 1996.
[51] Int. Cl.$^6$ .................. C12Q 1/68; C07H 21/04
[52] U.S. Cl. .................. 435/6; 536/23.5; 536/24.3
[58] Field of Search .................. 435/6, 91.2; 536/23.5, 536/24.33

[56] References Cited

PUBLICATIONS

Jazwinska and Powell Hemochromatosis and "HLA–H": definite! Hepatology. vol. 25(2):495–496, Feb. 1997.
Feder, et. al.. A novel MHC class I–like gene is mutated in patients with a hereditary haemochromatosis. Naure Genetics. vol. 13:399–408, Aug. 1996.
Bacon, B.R., "Causes of Iron Overload," N. Eng. J. Med. 326(2):126–127 (1992).
Cartwright, G.E. et al., "Inheritance of Hemochromatosis: Linkage to HLA," Trans. Assoc. Am. Phys. 91:273–281 (1978).
Edwards, C.Q. et al., "Screening for Hemochromatosis," N. Eng. J. Med. 328(22):1616–1619 (1993).
Finch, C.A., "Hemochromatosis—Treatment is Easy, Diagnosis Hard," West. J. Med. 153(3):323–325 (19980).
Gyapay, G. et al., "The 1993–94 Genethon human genetic linkage map," Nature Genetics 7:246–338 (1994).
Jazwinska, E.C. et al., "Localization of the Hemochromatosis Gene Close to D6S105," Am. J. Hum. Genet. 53:347–352 (1993).
Jazwinska, E.C. et al., "Haplotype Analysis oin Australian Hemochromatosis Patients: Evidence for a Predominant Ancestral Haplotype Exclusively Associated Hemochromatosis," Am. J. Hum. Genet. 56:428–433 (1995).
Lipinski, M. et al., "Idiopathic Hemochromatosis: Linkage with HLA," Tissue Antigens 11:471–474 (1978).
Lovett, M. et al., "Direct selection: A method for the isolation of cDNAs encoded by large genomic regions," Proc Natl. Acad. Sci. U.S.A. 88:9628–9632 (1991).
Nikiforov, T.T. et al., "Genetic Bit Analysis: a solid phase method for typing single nucleotide polymorphisms," Nucl. Acids Res. 22(20):4167–4175 (1994).
Phatak, P.D. et al., "Cost–effectiveness of Sceening for Hereditary Hemochromatosis," Arch. Intern Med. 154:769–776 (1994).
Simon,M. et al., "A Stody of 609 HLA Haplotypes Marking for the Hemochromatosis Gene: (1) Mapping of the Gene near the HLA–A Locus and Characters Required to Define a heterozygous Population and (2) Hypothesis Concerning the Underlying Cause of Hemochromatosis–HLA Association," Am. J. Hum. Genet. 41:89–105 (1987).

(List continued on next page.)

Primary Examiner—David Guzo
Assistant Examiner—William Sandals
Attorney, Agent, or Firm—Townsend and Townsend and Crew LLP

[57] ABSTRACT

A single base-pair polymorphism involving a mutation from Guanine (G), in individuals unaffected by the hereditary hemochromatosis (HH) gene defect, to Adeninc (A), in individuals affected by the HH gene defect is disclosed. The presence or absence of the polymorphic allele is highly predictive of whether an individual is at risk from HH: the polymorphism is present in 82% of affected individuals and only 4% of a random population screen. Methods of diagnosis, markers, and primers are disclosed and claimed in accordance with the present invention.

17 Claims, 3 Drawing Sheets

*24d1 Unaffected Sequence:*

5'-GGAAGAGCAGAGATATACGTGCCAGGTGGAGCACCCAGG-3'

(SEQ ID NO:1)

*24d1 Affected Sequence:*

5'-GGAAGAGCAGAGATATACGTACCAGGTGGAGCACCCAGG-3'

(SEQ ID NO:2)

OTHER PUBLICATIONS

Stone, C. et al., "Isolation of CA dinucleotide repeats close to D6S105; linkage disequilibrium with haemochromatosis," *Hum. Molec. Genet.* 3(11):2043–2046 (1994).

Summers, K.M. et al., "HLA Determinants in an Australian Population of Hemochromatosis Patients and Their Families," *Am. J. Hum. Genet.* 45:41–48 (1989).

Worwood, M. et al., "Alleles at D6S265 and D6S105 define a haemochromatosis-specific genotype," *Br. J. Haemat.* 86:863–866 (1994).

*24d1 Unaffected Sequence:*

5'-GGAAGAGCAGAGATATACGTGCCAGGTGGAGCACCCAGG-3'

(SEQ ID NO:1)

*24d1 Affected Sequence:*

5'-GGAAGAGCAGAGATATACGTACCAGGTGGAGCACCCAGG-3'

(SEQ ID NO:2)

FIGURE 1

*PCR Primers used for Amplification*

24d1.P1    (forward primer)

5'-TGGCAAGGGTAAACAGATCC-3'    (SEQ ID NO:5)

24d1.P2    (reverse primer)

5'-CTCAGGCACTCCTCTCAACC-3'    (SEQ ID NO:6)

*OLA Oligonucleotides*

*Upstream Oligonucleotides (5'-biotinylated)*

24d1.A    (common allele)

5'-bio-GGAAGAGCAGAGATATACGTG-3'    (SEQ ID NO:7)

24d1.B    (hemochromatosis allele)

5'-bio-GGAAGAGCAGAGATATACGTA-3'    (SEQ ID NO:8)

*Downstream Oligonucleotides (5'-phosphorylated)*

24d1.X    5'-p-CCAGGTGGAGCACCCAGG-dig-3'    (SEQ ID NO:9)

FIGURE 2

5'-TATTTCCTTCCTCCAACCTATAGAAGGAAGTGAAAGTTCCAGTCTTCCTGGCAA
GGGTAAACAGATCCCCTCTCCTCATCCTTCCTCTTTCCTGTCAAGTGCCTCCTTTG
GTGAAGGTGACACATCATGTGACCTCTTCAGTGACCACTCTACGGTGTCGGGCCT
TGAACTACTACCCCCAGAACATCACCATGAAGTGGCTGAAGGATAAGCAGCCAAT
GGATGCCAAGGAGTTCGAACCTAAAGACGTATTGCCCAATGGGGATGGGACCTAC
CAGGGCTGGATAACCTTGGCTGTACCCCTGGGGAAGAGCAGAGATATACGTGCC
AGGTGGAGCACCCAGGCCTGGATCAGCCCCTCATTGTGATCTGGGGTATGTGACT
GATGAGAGCCAGGAGCTGAGAAAATCTATTGGGGGTTGAGAGGAGTGCCTGAGG
AGGTAATTATGGCAGTGAGATGAGGATCTGCTCTTTGTTAGGGGGTGGGCTGAGG
GTGGCAATCAAAGGCTTTAACTT-3'                              (SEQ ID NO:3)

Figure 3a

5'-TATTTCCTTCCTCCAACCTATAGAAGGAAGTGAAAGTTCCAGTCTTCCTGGCAA
GGGTAAACAGATCCCCTCTCCTCATCCTTCCTCTTTCCTGTCAAGTGCCTCCTTTG
GTGAAGGTGACACATCATGTGACCTCTTCAGTGACCACTCTACGGTGTCGGGCCT
TGAACTACTACCCCCAGAACATCACCATGAAGTGGCTGAAGGATAAGCAGCCAAT
GGATGCCAAGGAGTTCGAACCTAAAGACGTATTGCCCAATGGGGATGGGACCTAC
CAGGGCTGGATAACCTTGGCTGTACCCCTGGGGAAGAGCAGAGATATACGTACC
AGGTGGAGCACCCAGGCCTGGATCAGCCCCTCATTGTGATCTGGGGTATGTGACT
GATGAGAGCCAGGAGCTGAGAAAATCTATTGGGGGTTGAGAGGAGTGCCTGAGG
AGGTAATTATGGCAGTGAGATGAGGATCTGCTCTTTGTTAGGGGGTGGGCTGAGG
GTGGCAATCAAAGGCTTTAACTT-3'                              (SEQ ID NO:4)

Figure 3b

5'-TATTTCCTTCCTCCAACCTATAGAAGGAAGTGAAAGTTCCAGTCTTCC<u>TGGCAA</u>

<u>GGGTAAACAGATCC</u>CCTCTCCTCATCCTTCCTCTTTCCTGTCAAGTGCCTCCTTTGGTG
   24d1.P1
AAGGTGACACATCATGTGACCTCTTCAGTGACCACTCTACGGTGTCGGGCCTTGA

ACTACTACCCCCAGAACATCACCATGAAGTGGCTGAAGGATAAGCAGCCAATGGA

TGCCAAGGAGTTCGAACCTAAAGACGTATTGCCCAATGGGGATGGGACCTACCAG

GGCTGGATAACCTTGGCTGTACCCCTGGGGAAGAGCAGAGATATACGTGCCAG

GTGGAGCACCCAGGCCTGGATCAGCCCCTCATTGTGATCTGGGGTATGTGACTGA

TGAGAGCCAGGAGCTGAGAAAATCTATTGGG<u>GGTTGAGAGGAGTGCCTGAG</u>GAG
                                    24d1.P2
GTAATTATGGCAGTGAGATGAGGATCTGCTCTTTGTTAGGGGGTGGGCTGAGGGT

GGCAATCAAAGGCTTTAACTT-3'                              (SEQ ID NO:3)

Figure 3c

5'-TATTTCCTTCCTCCAACCTATAGAAGGAAGTGAAAGTTCCAGTCTTCC<u>TGGCAA</u>

<u>GGGTAAACAGATCCC</u> CTCTCCTCATCCTTCCTCTTTCCTGTCAAGTGCCTCCTTTGG
   24d1.P1
TGAAGGTGACACATCATGTGACCTCTTCAGTGACCACTCTACGGTGTCGGGCCTT

GAACTACTACCCCCAGAACATCACCATGAAGTGGCTGAAGGATAAGCAGCCAATG

GATGCCAAGGAGTTCGAACCTAAAGACGTATTGCCCAATGGGGATGGGACCTACC

AGGGCTGGATAACCTTGGCTGTACCCCTGGGGAAGAGCAGAGATATACGTACC

AGGTGGAGCACCCAGGCCTGGATCAGCCCCTCATTGTGATCTGGGGTATGTGACT

GATGAGAGCCAGGAGCTGAGAAAATCTATTGGG<u>GGTTGAGAGGAGTGCCTGAGG</u>
                                     24d1.P2
AGGTAATTATGGCAGTGAGATGAGGATCTGCTCTTTGTTAGGGGGTGGGCTGAGG

GTGGCAATCAAAGGCTTTAACTT-3'                         (SEQ ID NO:4)

Figure 3d

HEREDITARY HEMOCHROMATOSIS DIAGNOSTIC MARKERS AND DIAGNOSTIC METHODS

This application is a continuation-in-part of U.S. Ser. No. 08/630,912, filed Apr. 4, 1996.

BACKGROUND OF THE INVENTION

1. Field of the Invention:

The invention relates to a genetic test for identifying subjects carrying one or two copies of a mutated gene causing hereditary hemochromatosis. More specifically, the invention concerns utilization of a new marker that has an allele in association with a common mutation in this gene which indicates the presence or absence of the mutation.

2. Background of the Technology:

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses. Neither the precise physiological mechanism of iron overaccumulation nor the gene which is defective in this disease is known.

HH is inherited as a recessive trait; in the current state of knowledge, heterozygotes appear asymptomatic and only homozygotes are affected by the disease. It is estimated that approximately 10% of individuals of Western European descent carry an HH gene mutation and that there are about one million homozygotes in the United States. Although ultimately HH produces debilitating symptoms, the majority of homozygotes have not been diagnosed. Indeed, it has been estimated that no more than 10,000 people in the United States have been diagnosed with this condition.

The symptoms of HH are often confused with those of other conditions, and the severe effects of the disease often do not appear immediately. Accordingly, it would be desirable to provide a method to identify persons who may be destined to ultimately become symptomatic in order to intervene in time to prevent excessive tissue damage. One reason for the lack of early diagnosis is the inadequacy of presently available diagnostic methods to ascertain which individuals are at risk.

Although blood iron parameters can be used as a screening tool, a confirmed diagnosis often employs liver biopsy which is undesirably invasive and costly. Thus, others have attempted to develop inexpensive and noninvasive diagnostics both for detection of homozygotes to confirm diagnosis in symptomatic individuals, provide presymptomatic detection so as to guide intervention in order to prevent organ damage, and for identification of heterozygote carriers.

The need for such diagnostics is documented, for example, in Finch, C. A. West J Med 153:323–325 (1990); McCusick, V. et al. Mendelian Inheritance in Man pp. 1882–1887, 11th ed., (Johns Hopkins University Press, Baltimore (1994)); Report of a Joint World Health Organization/Hemochromatosis Foundation/French Hemochromatosis Association Meeting on the Prevention and Control of Heraochromatosis, 1993; Edwards, C. Q. et al. New Engl J Med328:1616–1620 (1993); Bacon, B. R. New Engl J Med326:126–127 (1992); Balan, V. et al. Gastroenterology 107:453–459 (1994); Phatak, P. D. et al. Arch Int Med 154:769–776 (1994).

Although the gene carrying the mutation or mutations that cause HH is at present unknown, genetic linkage studies in HH families have shown that the gene that causes the majority of disease in Caucasians resides on chromosome 6 near the HLA region at 6p21.3 (Cartwright, Trans Assoc Am Phys 91:273–281 (1978); Lipinski, M. et al. Tissue Antigem 11:471–474 (1978)). It is believed that within this gene a single mutation gives rise to the majority of disease-causing chromosomes present in the popuhtion today. McCusick, V. et al. supra. This is referred to herein as the "common" or "ancestral" or "common ancestral" mutation. These terms are used interchangeably. It appears that about 80% to about 90% of all HH patients carry at least one copy of a common ancestral mutation which carries with it specific forms of certain genetic markers close to this ancestral HH gene defect. These markers are, as a first approximation, in the allelic form in which they were present at the time the HH mutation occurred. See, for example, Simon, M. et al. Am J Hum Genet 41:89–105 (1987); Jazwinska, E. G. et al. Am J Hum Genet 53:242–257 (1993); Jazwinska, E. G. et al. Am J Hum Genet 56:428–433 (1995); Worwood, M. et al. Brit J Hematol 86:833–846 (1994); Summers, K. M. et al. Am J Hum Grenet 45:41–48 (1989).

Although each of such markers is putatively useful in identifying individuals carrying this defective HH gene, of course, crossing over events have, over time, separated some of the ancestral alleles from the relevant genetic locus that is responsible for HH. Therefore, no single marker of the types described above in Simon, M. et at. supra.; Jazwinska, E. C. et al. (1993) supra.; Jazwinska, E. C. et at. (1995) supra.; Worwood, M. et at. supra.; Summers, K. M. et at. is currently close enough and thus specific enough to identify individuals carrying the ancestral HH mutation.

Several markers at the approximate location of the gene associated with HH have been described. Gyapay, G. et al. Nature Genetics 7:246–339 (1994) describe the markers D6S306 and D6S258 which have been demonstrated to be in the region of the HH gene. These markers consist of microsatellite regions containing $(CA)_n$ repeats of various lengths. Worwood, M. et al. Brit J Hematol 86:833–846 (1994) (supra) describes an allele at D6S265 and Jazwinska, E. C. et al. Am J. Hum Genet 53:242–257 (1993) (supra) describes D6S105 as associated with an HH-specific genotype. Stone, C. et al. Hum Molec Genet 3:2043–2046 (1994) describes an additional HH associated aHele at D6S100I. In copending U.S. patent application Ser. No. 08/632,673, filed on Apr. 4, 1996, which is hereby incorporated by reference in its entirety, a polymorphism, designated 24d1, is described in detail. In co-pending U.S. patent application Ser. No. 08/599,252, filed Feb. 9, 1996, which is a continuation-in-part of U.S. patent application Ser. No. 08/559,302, filed Nov. 15, 1995, which is a continuation-in-part of U.S. patent application Ser. No. 08/436,074, filed May 8, 1995, the disclosures of which are hereby incorporated by reference in their entirety, a plurality of additional markers are disclosed comprising the following alleles: microsatellite repeat alleles 19D9:205; 18B4:235; 1A2:239; 1E4:271; 24E2:245; 2B8:206; 3321-1:197; 4073-1:182; 4440-1:180; 4440-2:139; 731-1:177; 5091-1:148; 3216-1:221, 4072-2:148; 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, prior art allelic markers D6S258:199, D6S265:122, D6S105:124, D6S306:238, D6S464:206; and D6S1001:180, and/or alleles associated with the HHP-1, the HHP-19 or HHP-29 single base-pair polymorphism. In the notation employed for the microsatellite repeat alleles, the number subsequent to the colon indicates the number of nucleotides in the HH-associated allele between and including the flanking primers when the primers are those illustrated therein.

As described hereinbelow, a single base-pair polymorphism associated with the HH gene has been identified, which can be used by itself or included in additional diagnostic genotypes. A highly informative association of this polymorphism with the ancestral HH gene has also been found permitting the detection of genotypes with very high probabilities of being associated with the presence of the common HH mutated gene.

The diagnostic genotype described below as associated with HH is uncommon in the general population, consistent with estimates of the frequency of the HH gene mutation. However, it is present in a large majority of individuals affected by HH. Accordingly, the presence or absence of this genotypo can be used as a rapid, inexpensive and noninvasive method to assess an individual for the presence or absence of the common version of the defective HH gene.

SUMMARY OF THE INVENTION

In one aspect of the present invention there is provided a convenient method to assess individuals for the presence or absence, or the likelihood of said presence or absence, of a common lift associated mutation using genetic techniques that are readily applied noninvasively. Only a sample containing the cells including genomic DNA (or optionally, as discussed below in Example 5, RNA) from the subject to be tested is required. In accordance with other aspects of the present invention, materials and kits useful in conducting the genetic tests are provided. The allclio variant reported herein represents an improved marker for the HH gene, and is marked by a specific single base-pair difference in DNA sequence (referred to herein as a "base-pair polymorphism" and/or "24d1").

Thus, in accordance with the first aspect of the present invention, there is provided a method to determine with improved likelihood the presence or absence of the common hereditary hemochromatosis HH gene mutation in an individual, which method comprises obtaining genomic DNA from the individual and assessing the DNA for the presence or absence of a single base-pair polymorphism represented by the markers comprising the DNA sequences of SEQ ID NO: 1 and SEQ ID NO:2, as shown in FIG. 1. In such sequences, a Guanine (G) is present in the unaffected DNA sequence (SEQ ID NO:1) and an Aderfine (A) is present in the "affected DNA sequence" (SEQ ID NO:2). As used herein, the term "affected DNA sequence" refers to a DNA sequence that is associated with the common ancestral ItH gene mutation. An "affected" individual refers to an individual diagnosed as having HH. The term "unaffected" or "random" DNA sequence refers to DNA sequences taken from random individuals who are not known to be affected with HH, such individuals are sometimes referred to herein as "unaffected" or "random" individuals.

The presence of the A allele of this polymorphism, as shown in the "affected sequence" shown in Example 2, is highly indicative of the presence of the common HH gene mutation in the genome of the individual. The absence of the A allele of this polymorphism is indicative of the absence of the common HH gene mutation in the genome of said individual. Moreover, the presence of the A rather than G allele of this polymorphism is highly indicative of the presence of the common ancestral genetic HH defect. The use of the 24d1 polymorphism as a marker represents an improvement over that provided by the multiple alleles identified through the screening for additional markers, such as the microsatellite (CA) repeat alleles and single base-pair polymorphisms identified above. Nevertheless, screening of an individual's genomic DNA can be accomplished in connection with the G to A polymorphism in accordance with the present invention in combination with one or more marker (i.e., one, two, three, four, five, etc.) alleles described in any of U.S. patent application Ser. Nos. 08/599,252, 08/559,302, and 08/436,074.

Upon identification of the HH associated 24d1 A allele of the present invention in a sample of DNA from an individual, particularly in combination with the presence of one or more HH-mutation-associated CA repeat alleles and/or the single base pair polymorphisms identified above, there is a high likelihood that the common HH mutant gene is present.

Thus, the invention is directed to a method to determine the presence or absence of the common hereditary hemochromatosis (HH) gene mutation in an individual, which method comprises obtaining genomic DNA (or RNA) from the individual; and assessing the DNA (or RNA) for the presence or absence of the HH-associated allele of the base-pair polymorphism designated herein by the unique sequence in the human genome; wherein the absence of the HH associated allele indicates the likelihood of the absence of the ancestral HH gene mutation in the genome of the individual and the presence of the HH-associated allele indicates the likelihood of the presence of the HH gene mutation in the genome of the individual. The method could also include determining a genotype which is a combination of the 24dl allele with an HH-associated microsatellite repeat allele.

The invention is further directed to DNA primer pairs for PCR amplification that flank the microsatellite repeat alleles and that flank the base-pair polymorphism markers useful in the method of the invention and to kits containing these primer pairs. The invention is also directed to oligonucleotides permitting determination of base-pair polymorphisms by oligonucleotide ligation assay (OLA) or by alternative methods. The invention is also directed to use of the nucleotide sequence information around the base-pair polymorphism to design additional primer pairs for amplification. Applicants have provided sequence information in either direction of the single base-pair difference at 24d1. As will be appreciated to those of skill in the art, the availability of this sequence information provides additional opportunities for the design of primers for amplification of the relevant portion of DNA.

Accordingly, the invention is also directed to primers designed on the basis of this sequence information and to a computer-readable medium having recorded thereon the nucleotide sequences set forth in FIG. 1 as described below or fragments thereof. The claimed fragments are those that do not coincide with nucleotide sequences presently available to the public in computer-readable form.

In accordance with a first aspect of the present invention, there is provided a method to determine the presence or absence of the common hereditary hemochromatosis (HH) gene mutation in an individual, comprising: providing DNA or RNA from the individual, and assessing the DNA or RNA for the presence or absence of the HH-associated allele A of a base pair polymorphism designated herein 24d1, wherein, as a result, the absence of the allele indicates a likely absence of the HH gene mutation in the genome of the individual and the presence of the allele a likely presence of the HH gene mutation in the genome of the individual.

In another embodiment, the assessing step further comprises assessing the DNA or RNA for the presence or absence of any one of the following HH-associated alleles of base pair polymorphisms HHP1, HHP-19, or HHP-29, wherein, as a result, the presence of the 24d1 allele in combination with the presence of at least one of the base pair polymorphisms HHP-1, HHP-19, or HHP-29 indicates the likely presence of the HH gene mutation in the genome of the individual and the absence of 24d1 allele in combination with the absence of any one or all of the base pair polymorphisms HHP-1, HHP-19, or HHP-29 indicates a likely absence of the HH gene mutation in the genome of the individual. In another embodiment, the assessing step further comprises assessing the DNA or RNA for the presence or absence of any one of the following alleles defined by markers having microsatellite repeats, wherein the number subsequent to the colon indicates the number of nucleotides between and including the flanking oligonucleotide primers when the oligonucleotide primers are those exemplified herein: 19D9:205; 18B4:235; 1A2:239; 1E4:271; 24E2:245; 2B8:206; 3321-1:197; 4073-1:182; 4440-1:180; 4440-2:139; 731-1:177; 5091-1:148; 3216-1:221, 4072-2:148; 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, D6S258:199, D6S265:122, D6S105:124, D6S306:238, D6S464:206; and D6S1001:180, wherein, as a result, the presence of the 24d1 A allele in combination with the presence of at least one microsatellite repeat allele indicates the likely presence of the HH gene mutation in the genome of the individual and the absence of the 24d1 A allele in combination with the absence of any one or all of the microsatellite repeat alleles indicates the likely absence of the HIt gene mutation in the genome of the individual. In another embodiment, the assessing step further comprises assessing the DNA or RNA for the presence or absence of any one of the following alleles defined by markers having microsatellite repeats, wherein the number subsequent to the colon indicates the number of nucleotides between and including the flanking oligonucleotide primers when the oligonucleotide primers are those exemplified herein: 19D9:205; 18B4:235; 1A2:239; 1E4:271; 24E2:245; 2B8:206; 3321-1:197; 4073-1:182; 4440-1:180; 4440-2:139; 731-1:177; 5091-1:148; 3216-1:221, 4072-2:148; 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, D6S258:199, D6S265:122, D6S105:124, D6S306:238, D6S464:206; and D6S1001:180, wherein, as a result, the presence of the 24d1 allele in combination with the presence of at least one of the base pair polymorphisms HHP-1, HHP-19, or HHP-29 in further combination with the presence of at least one of the microsatellite repeat alleles indicates the likely presence of the HH gene mutation in the genome of the individual and the absence of 24d1 allele in combination with the absence of any one or all of the base pair polymorphisms HHP-1, HHP-19, or HHP-29 in further combination with the absence of any one or all of the microsatellite repeat alleles indicates the likely absence of the HH gene mutation in the genome of the individual. In another embodiment, the assessing step is performed by a process which comprises subjecting the DNA or RNA to amplification using oligonucleotide primers flanking the base-pair polymorphism 24d1. In another embodiment, the assessing step is performed by a process which comprises subjecting the DNA or RNA to amplification using oligonucleotide primers flanking the base-pair polymorphism 24d1 and oligonucleotide primers flanking at least one of the base-pair polymorphisms HHP-1, HHP-19, and HHP-29. In another embodiment, the assessing step is performed by a process which comprises subjecting the DNA or RNA to amplification using oligonucleotide primers flanking the base-pair polymorphism 24d1 and oligonucleotide primers flanking at least one of the microsatellite repeat alleles. In another embodiment, the assessing step is performed by a process which comprises subjecting the DNA or RNA to amplification using oligonucleotide primers flanking the base-pair polymorphism 24d1, oligonucleofide primers flanking at least one of the base-pair polymorphisms HHP-1, HHP-19, and HHP-29, and oligonucleotide primers flanking at least one of the microsatellite repeat alleles.

In accordance with a second aspect of the present invention, there is provided a set of oligonucleotides for use in an oligonucleotide ligation assay determination of the presence or absence of an HH-1-associated allele of a base-pair polymorphism, wherein the base pair polymorphism comprises 24d1 and the oligonucleotides comprise the sequences of SEQ ID NO:7, SEQ 112) NO:8, and SBQ ID NO: 9.

In accordance with a third aspect of the present invention, there is provided a kit for the detection of the presence or absence of an HH-associated allele of a base-pair polymorphism, the base-pair polymorphism comprising 24d1, as designated herein, the kit comprising the above oligonucleotide primer set. In another embodiment, the kit further comprises oligonucleotide primers for amplifying the DNA containing the base-pair polymorphism.

In accordance with a fourth aspect of the present invention, there is provided a method to evaluate potential responsiveness of an individual infected with hepatitis C to intefferon treatment, comprising determining the presence or absence of the common hereditary hemochromatosis gene in the individual according to any of the above methods.

In accordance with a fifth aspect of the present invention, there is provided a computer readable medium having recorded thereon the nucleotide sequences of any one of SEQ ID NO:1, SEQ ID NO:2, SEQ ID NO:3, and SEQ ID NO: 4 and any novel fragments thereof.

In accordance with a sixth aspect of the present invention, there is provided An oligonucleotide primer useful for amplification of DNA, the oligonucleotide primer designed on the basis of the DNA sequence of any one of SEQ ID NO:1, SEQ ID NO:2, SEQ ID NO:3, and SEQ 1212) NO:4.

In accordance with a seventh aspect of the present invention, there is provided A genetic marker predictive of a hereditary hemochromatosis (HH) gene mutation comprising a partial sequence of the human genome including at least 16 contiguous nucleotide residues including "X" in the following nucleotide sequence:

5'-GGAAGAGCAGAGATATACGTXCCAGGTGGAGCACCCAGG-3'

(SEQ ID NO: 10)

and sequences complementary therewith, wherein "X" represents a single base-pair polymorphism of G in a population unaffected with the HH gene mutation and A in a population affected with the HH gene mutation.

In accordance with an eighth aspect of the present invention, there is provided a genetic marker predictive of a hereditary hemochromatosis (HH) gene mutation comprising a partial sequence of the human genome including at least 16 contiguous nucleotide residues including "X" in the following nucleotide sequence:

```
5'- TATTTCCTTCCTCCAACCTATAGAAGGAAGTGAAAGTTCCAG

TCTTCCTGGCAAGGGTAAACAGATCCCCTCTCCTCATCCTTC

CTCTTTCCTGTCAAGTGCCTCCTTTGGTGAAGGTGACACATC

ATGTGACCTCTTCAGTGACCACTCTACGGTGTCGGGCCTTGA

ACTACTACCCCAGAACATCACCATGAAGTGGCTGAAGGATA

AGCAGCCAATGGATGCCAAGGAGTTCGAACCTAAAGACGTA

TTGCCCAATGGGGATGGGACCTACCAGGGCTGGATAACCTTG

GCTGTACCCCCTGGGGAAGAGCAGAGATATACGTXCCAGGT

GGAGCACCCAGGCCTGGATCAGCCCCTCATTGTGATCTGGGG

TATGTGACTGATGAGAGCCAGGAGCTGAGAAAATCTATTGGG

GGTTGAGAGGAGTGCCTGAGGAGGTAATTATGGCAGTGAGA

TGAGGATCTGCTCTTTGTTAGGGGGTGGGCTGAGGGTGGCAA

TCAAAGGCTTTAACTT-3'
```

(SEQ ID NO: 13)

and sequences complementary therewith, wherein "X" represents a single base-pair polymorphism of G in a population unaffected with the HH gene mutation and A in a population affected with the HH gene mutation.

In accordance with a ninth aspect of the present invention, there are provided reverse complementary sequences of any one of the sequences of SEQ ID NO:1 through SEQ ID NO: 13.

BRIEF DESCRIPTION OF THE DRAWING FIGURES

FIG. 1 shows sequence information SEQ. ID NO: 1–2 relating to the portions of the genome surrounding the 24d1 polymorphism of the present invention.

FIG. 2 shows the oligonucleotide sequences SEQ. ID NO: 5–9 used for amplification and OLA determination of the 24d1 base-pair polymorphism of the present invention.

FIG. 3 (Parts A–D) shows a 517 base sequence representing the genomic DNA sequence surrounding the 24d1 polymorphism of the present invention. FIG. 3a provides the sequence infomation SEQ. ID NO: 3 for the G allde (unaffected), FIG. 3b provides the sequence information SEQ. ID NO: 4 for the A allele (affected), FIG. 3c shows the position of the polymorphism in the G allele and the potions of the sequence SEQ. ID NO: 3 used for the design of the primers illustrated in FIG. 2, and FIG. 3d shows the position of the polymorphism in the A allele and the portions of the sequence SEQ. ID NO: 4 used for the design of the primers illustrated in FIG. 2.

DETAILED DESCRIPTION OF THE INVENTION

The inventors of the present invention have discovered an allele of a single base-pair polymorphism that is present in a highly significant percentage of the gertemie DNA of individuals affected with hereditary hemochromatosis (HH) while only present in a small percentage of individuals who are not known to be affected by the disease. Specifically, the allele is detected in about 82% of the chromosomes of affected individuals and in only 4% of random chromosomes. The term "random chromosomes" as used herein refers to chromosomes from individuals who are not known to be affected with HH. The term "affected chromosomes" as used herein refers to chromosomes from individuals who have been diagnosed as having HH.

As mentioned above, the single base-pair polymorphism of the present invention comprises a Guanine (G) to Adenine (A) substitution, where Guanine (G) is present in the unaffected DNA sequence and Adenine (A) is present in the affected DNA sequence. The polymorphism of the present invention, referred to herein as 24d1, is illustrated in FIG. 1 and represented by SEQ ID NO: 1 (unaffected) and SEQ ID NO:2 (affected).

The A allele of the single base-pair polymorphism of the present invention is present in the DNA of only 4% of random chromosomes. In contrast, previously identified allelic markers are often present in the DNA of random chromosomes at higher frequencies, up to greater than 50%. The low frequency of the A allele, together with the high frequency of G in affected chromosomes, makes 24d1 a superior marker for the common HH mutation.

Approximately 1 individual out of every 10 individuals are presently believed to be carriers of the HH mutant gene. Thus, about 1 out of every 20 chromosomes in a random screen, or 5%, should contain a mutant HH gene. The present single base-pair polymorphism with its 4% prevalence in random chromosomal screening, in addition to its occurrence in 82% of the chromosomes from individuals known to be affected with HH, indicates that the polymorphism is highly predictive of the presence or absence of the mutant HH gene as opposed to a random occurrence.

As used herein, "marker" refers to a DNA sequence polymorphism flanked by conserved regions. Conserved regions flanking the "marker" can be utilized for the design and construction of primers for amplifying the relevant DNA portions. In some cases, two sets of oligonucleotides will be required: one set to amplify the general region of the DNA of interest and the other set to perform OLA determination of the DNA sequence polymorphism.

The frequency of the present HH-associated allele is approximately 4% in random individuals, which is consistent with the estimates of the gene frequency in the general caucasian population. This is to be expected since approximately one in about ten individuals is a carrier of the common ancestral mutation and is clinically normal and will remain so.

Shown in FIG. 1 are nucleotide sequences on either side of the marker described herein. The Figure shows the relevant sequence surrounding the polymorphism. In addition, FIG. 3 provides more extensive sequence information relating to the nucleotide sequence surrounding the 24d1 polymorphism of the present invention. In FIG. 3, a sequence comprising 517 base-pairs representing the genomic DNA sequence surrounding the 24d1 polymorphism is provided. As will be appreciated, certain random polymorphisms may exist, and are to be expected, within such sequence as among various individuals. However, the overall sequence appears highly conserved. Thus, it will be appreciated that the sequence represented by SEQ ID NO:3 as shown in FIG. 3, any portions or subsets thereof, and such minor mutations, polymorphisms, and the like, are all highly useful in accordance with the present invention and are, as such, contemplated herein. FIG. 3a shows the sequence surrounding the 24d1 G allele (SEQ ID NO:3) (unaffected) as highlighted in FIG. 3c; FIG. 3b shows the sequence surrounding the 24d1 A allele (SEQ ID NO: 4) (affected) as highlighted in FIG. 3d.

All of the sequences mentioned herein are of sufficient length that it is convenient to provide them in computer-readable medium. Examples of computer-readable media include those that are well known in the art such as floppy disks, hard disks, random access memory (RAM), read only memory (ROM), and CD-ROM. Another aspect of the invention is directed to computer-readable media having recorded thereon the nucleotide sequence depicted in FIG. 1 or any portion of such sequence therein, to the extent that the portion is novel—i.e., does not currently exist in computer-readable form.

The single base-pair polymorphism of the present invention describes an allele which is present in high proportions on chromosomes of affected individuals. This base-pair polymorphism, designated 24d1, was discovered in the course of sequencing a gene isolted from the relevant portion of chromosome 6 derived from affected as compared to unaffected individuals. This sequence resides approximately 1.5 megabases telomeric of the known marker D6S105. See Jazwinska, E. C. et at. (1993), supra. The precise nature of the base-pair polymorphism is set forth in the examples hereinbelow. The presence of one allele, especially in combination with any one of the characteristic allclio variants among the microsatellite repeat markers and/or the single base-pair polymorphisms described and characterized in any one of copending applications, Ser. Nos. 08/599,252, 08/559,302, and 08/436,074, or characterized in the prior art indicates the presence of the common HH mutation.

To perform a diagnostic test for the presence or absence of the HH gene in an individual, a suitable genomic DNA-containing sample from a subject is obtained and the DNA extracted using conventional techniques. It will be readily appreciated that appropriate RNA samples can also be utilized in accordance with the present invention for the detection of the 24d1 polymorphism. An illustration of the use of RNA for such detection is provided in Example 5, below. In the present text, however, the majority of the discussion is directed to the use of DNA from individuals because of its ease of isolation and the like.

For example, DNA can be prepared by standard methods. See Dracopoli, H. et al. infra.). Most typically, a blood sample, a buccal swab, a hair follicle preparation or a nasal aspirate is used as a source of cells to provide the DNA. The extracted DNA is then subjected to amplification, for example, using the polymerase chain reaction (PCR) according to standard procedures. The allele of the single base-pair polymorphism is determined by conventional methods including manual and automated fluorescent DNA sequencing, primer extension methods (Nikiforov, T. T. et al. Nucl Acids Res 22:4167–4175 (1994)), oligonucleotide ligation assay (OLA) (Nickerson, D. A. et al. Proc Natl Acad Sci USA 87:8923–8927 (1990)), allele-specific PCR methods (Rust, S. et at. Nucl Acids Res 6:3623–3629 (1993)), RNase mismatch cleavage, single strand conformation polymorphism (SSCP), denaturing gradient gel electrophoresis (DGGE), and the like.

As will further be described in Examples 1 and 2, one genotype associated with HH is defined by the A allele at 24d1. The absence of this genotype indicates the absence of the ancestral HH gene mutation in the genome of said individual and the presence of said genotype indicates the presence of said HH gene mutation.

In addition to the genotype described above, as described in any of copending applications, Ser. Nos. 08/594,252, 08/559,302, and 08/436,074, genotypes characterized by the presence of the alldes 19D9:205; 18B4:235; 1A2:239; 1E4:271; 24E2:245; 2B8:206; 3321-1:197; 4073-1:182; 4440-1:180; 4440-2:139; 731-1:177; 5091-1:148; 3216-1:221, 4072-2:148; 950-1:142; 950-2: 164; 950-3: 165; 950-4:128; 950-6:15 1; 950-8:137; 63-1:151; 63-2:113; 63-3:169; 65-1:206; 65-2:159; 68-1:167; 241-5:108; 241-29:113; 373-8:151; and 373-29:113, alleles D6S258: 199, D6S265: 122, D6S105: 124, D6S306:238, D6S464:206; and D6S 1001: 180, and/or alleles associated with the HHP-1, the HHP-19 or HHP-29 single base-pair polymorphism can also be used to assist in the identification of an individual whose genome contains the common HH mutation. As discussed in Example 4, below, the marker of the present invention can be utilized for the detection of, and differentiation of, individuals who are homozygous and heterozygous for the HH-gene mutation. The value of identifying individuals who carry two copies of the A allele (i.e., individuals who are likely to be homozygous for the HH-gene mutation) is that such individuals can then initiate therapy (currently phlebotomy) to reduce iron stores in the body, and beneficially alter the course of the disease.

The presence of the HIt genotype also has predictive power with respect to certain therapeutic regimes where it is understood that the effectiveness of these regimes is related to the HIt genotype. For example, it has been disclosed that the potential for hemochromatosis interferes with the effectiveness of interferon treatment of hepatitis C (Bacon, B. Abstracts of the Fifth Conference of the International Association for the Study of Disorders of Iron Metabolism 15–16 (1995)). Thus, knowledge of the status of the genotype of the subject with respect to the I-IH mutation provides guidance in designing therapeutic protocols and/or regimens for use in connection with other diseases. As the correlations between treatment regimens and iron metabolism continue to become established, the diagnostic methods of the invention provide a useful tool in designing therapeutic protocols consistent with the presence or absence of the common HB mutation.

As will be readily understood and appreciated by those of ordinary skill in the art, with respect to any sequences disclosed herein, complimentary sequences, reverse complimentary sequences, and/or other similar sequence information are equivalent to the disclosed sequences and are therefore contemplated in accordance with the present invention.

The following examples are intended to illustrate but not to limit the invention.

EXAMPLE 1

Identification of the Marker for HH

As described in any of co-pending applications, Ser. Nos. 08/599,252, 08/559,302, and 08/436,074, clones containing the relevant sequences were retrieved in a genome walking strategy beginning with the previously described markers D6S306, D68105 and D68258. Standard chromosome-walking techniques are described in Sambrook, J. et al. Molecular Cloning—A Laboratory Manual (2nd Ed., Cold Spring Harbor Laboratory Press, New York (1989)) and in Dracopoli, H. et al. eds. Current Protocols in Human Genetics (J. Wiley & Sons, New York (1994)).

A number of coding sequences in the HH region of the genome were identified by direct selection procedures. See Lovett, M et al. Proc. Natl Acad Sci USA 88:9628–9632 (1991). One gene sequence that was identified using this process was identified at a position approximately 1.5 megabases telomeric of the known marker D6S105. See Jazwinska, E. C. et al. (1993), supra. Such sequence was used to obtain cDNA clones which encode the full length gene, designated cDNA 24. The sequence of this gene was determined in a random individual and an individual affected with HH. When these sequences were compared, a base-pair difference was noted, as illustrated in Example 2 below. The base-pair difference was designated 24d1.

EXAMPLE 2

Single Base-Pair Polymorphism: 24d1

Base-pair polymorphism 24d1 was determined as described in Example 1. The genomic sequence surrounding the polymorphism is highly, if not entirely, conserved and the sequence for each of the affected and unaffected populations is provided below:

24d1 Unaffected Sequence:

5'-GGAAGAGCAGAGATATACGTGCCAGGTGGAGCACCCAGG-3'

(SEQ ID NO: 1)

24d1 Affected Sequence:

5'-GGAAGAGCAGAGATATACGTACCAGGTGGAGCACCCAGG-3'

(SEQ ID NO: 2)

FIG. 2 shows the sequences of primers used for amplification and sequencing of the above base-pair polymorphism. The amplification primers for 24d1 are labeled 24d1.P1 (SEQ ID NO:5) and 24d1.P2 (SEQ ID NO:6). The oligonucleofides used in the sequence determination by OLA for 24d1 are designated 24d1.A (SEQ ID NO:7), 24d1.B (SEQ ID NO:8), and 24d1.X (SEQ ID NO:9). As indicated in the sequences shown, "bio" indicates biofin coupling, "p" indicates 5'-phosphate, and "dig" indicates coupled digoxigenin. It will be appreciated that the binding of biotin and digoxigenin can be reversed. In other words, digoxigenin can be bound to the 5' end of 24d1.A and 24d1.B and biotin can be bound to the 3' end of 24d1.X.

Table 1 shows the frequency of this single base pair polymorphism in chromosomes from affected and random individuals:

TABLE 1

| Frequencies of Alleles as % of Chromosomes Tested | | |
|---|---|---|
| | Affected Chromosomes (N = 258) | Random Chromosomes (N = 268) |
| 24d1 "A" | 82% | 4% |
| 24d1 "G" | 18% | 96% |

The allele in 24d1:A occurs in 82% of the affected chromosomes; its occurrence at 4% in random chromosomes approximates the estimated frequency of the common HH mutation in the general population.

EXAMPLE 3

24d1 Polymorphism Gene Probes and Marker

Sequences surrounding and overlapping the single base-pair polymorphism of the present invention can be utility for a number of gene mapping, targeting, and detection procedures. For example, genetic probes can be readily prepared for hybridization and detection of the 24d1 polymorphism. As will be appreciated, probe sequences are preferably greater than about 16 or more oligonucleotides in length and possess sufficient complementarity to distinguish between the G (in unaffected chromosomes) and A (in affected chromosomes). Similarly, such sequences surrounding and overlapping the single base-pair polymorphism of the present invention can be utilized in allde specific hybridization procedures.

It will be appreciated by those of ordinary skill in the art that the sequence surrounding and overlapping the polymorphism of the present invention or any portion or subset thereof that allows one to identify the polymorphism is highly useful. Thus, in accordance with another aspect of the present invention there is provided a genetic marker predictive of a hereditary hemochromatosis (HH) gene mutation comprising a partial sequence of the human genome including at least about 16 contiguous nucleotide residues including "X" in the following nucleotide sequence:

5'-GGAAGAGCAGAGATATACGTXCCAGGTGGAGCACCCAGG-3'

(SEQ ID NO: 10)

and sequences complementary therewith, wherein "X" represents a single base-pair polymorphism of G in a population unaffected with the HH gene mutation and A in a population affected with the HH gene mutation.

EXAMPLE 4

Differentiation of Individuals who are Homozygous Versus Heterozygous for the 24d1 Polymorphism As will be appreciated, the OLA assay allows the differentiation between individuals who are homozygotous versus heterozygotous for the 24d1 polymorphism. This feature allows one to rapidly and easily determine whether an individual is at a significant risk of developing HH.

In the OLA assay, when carded out in microtiter plates, for example, one well is used for the determination of the presence of the 24d1:G allele and a second well is used for the determination of the presence of the 24d1:A allele. Thus, the results for an individual who is heterozygous for the 24d1 polymorphism will show a signal in each of the A and G wells and an individual who is homozygous for the 24d1 polymorphism will show a signal in only the A well. Those individuals who are homozygous for the A allele at 24d1 are, as discussed above, likely homozygous for the common ancestral HH-mutation and are at a significant risk of developing HH.

EXAMPLE 5

Detection of the 24d1 Polymorphism in RNA

As mentioned above, RNA from an individual (i.e., freshly transcribed or messenger RNA) can be easily utilized in accordance with the present invention for the detection of the 24d1 polymorphism. Total RNA from an individual can be isolated according to the procedure outlined in Sambrook et al., supra., the disclosure of which is hereby incorporated by reference. The use of RNA, as opposed to DNA, follows essentially an identical approach: the RNA is isolated and after reverse transcription the characteristic G to A polymorphism is detected. In order to perform PCR amplification of the RNA prior to OLA assay, the following oligonucleotide primers are preferably utilized:

Forward Primer

24d1.P3  CTG AAA GGG TGG GAT CAC AT
(SEQ ID NO: 11)

Reverse Primer

24d1.P4  CAA GGA GTT CGT CAG GCA AT
(SEQ ID NO: 12)

INCORPORATION BY REFERENCE

To the extent that any reference (including books, articles, papers, patents, and patent applications) cited herein is not already incorporated by reference, they are hereby expressly incorporated by reference in their entirety.

EQUIVALENTS

While the invention has been described in connection with specific embodiments therof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

---

What is claimed is:

1. A method to determine the presence or absence of the common hereditary hemochromatosis (HH) gene mutation in an individual, comprising:

providing DNA or RNA from the individual; and assessing the DNA or RNA for the presence or absence of the HH-associated allele A of a base pair polymorphism designated herein 24d1, wherein, as a result, the absence of the allele indicates a likely absence of the HH gene mutation in the genome of the individual and the presence of the allele a likely presence of the HH gene mutation in the genome of the individual.

2. The method of claim 1, wherein the assessing step is performed by a process which comprises subjecting the DNA or RNA to amplification using oligonucleotide primers flanking the base-pair polymorphism 24d1.

3. The method of claim 2, wherein the assessing step further comprises an oligonucleotide ligation assay.

4. The method of claim 3, wherein the assessing step further comprises providing a housing having a first well that is adapted for conducting an oligonucleotide ligation assay and providing a first signal when the A allele of the 24d1 polymorphism is present in the DNA or RNA and a second well that is adapted for conducting an oligonucleotide ligation assay and providing a second signal when the G allele of the 24d1 polymorphism is present in the DNA or KNA.

5. The method of claim 4, wherein the assessing step further comprises detecting whether the DNA or RNA is homozygous or heterozygous for the 24d1 polymorphism, wherein when the DNA or RNA is heterozygous for the 24d1 polymorphism the first and second signal will be observed upon conducting the oligonucleotide ligation assay and when the DNA or RNA is homozygous for the 24d1 polymorphism only the first signal will be observed upon conducting the oligocnucleotide ligation assay.

6. The method of claim 3, wherein DNA is amplified with oligonucleotide primers of SEQ ID NO:5 and SEQ ID NO:6.

7. The method of claim 6, wherein the oligonucleotide ligation assay is accomplished using oligonucleotides of SEQ ID NO:7, SEQ ID NO:8, and SEQ ID NO:9.

8. The method of claim 3, wherein RNA is amplified with oligonucleotide primers of SEQ ID NO: 11 and SEQ ID NO: 12.

9. The method of claim 8, wherein the oligonuceotide ligation assay is accomplished using oligonucleotides of SEQ ID NO:7, SEQ ID NO:8 and SEQ ID NO:9.

10. A method to evaluate potential responsiveness of an individual infected with hepatitis C to interferon treatment, comprising determining the presence or absence of the common hereditary hemochromatosis gene in the individual according to the method of any one of claims 1–9 wherein the potential responsiveness of an individual infected with hepatitis C is determined.

11. A set of oligonucleotides for an oligonucleotide ligation assay determination of the presence or absence of an HH-associated allele of a base-pair polymorphism, wherein the base pair polymorphism comprises 24d1 and the oligonucleotides comprise the sequences of SEQ ID NO:7, SEQ ID NO:8, and SEQ ID NO:9.

12. A kit for the detection of the presence or absence of an HH-associated allele of a base-pair polymorphism, the base-pair polymorphism comprising 24d1, as designated herein, the kit comprising the oligonucleotide primer set of SEQ ID NO: 5, 7, 8, 9, 11, 12.

13. The kit of claim 12, further comprising primers for amplifying the DNA containing the base-pair polymorphism designated hrein 24d1.

14. An oligonucleotide primer which is complementary to a DNA sequence selected from the group consisting of SEQ ID NO: 1, SEQ ID NO:2, SEQ ID NO:3, and SEQ ID NO:4.

15. A genetic market predictive of a hereditary hemochromatosis (HH) gene mutation comprising a partial sequence of the human genome including at least 16 contiguous nucleotide resiues including "X" in the following nucleotide sequence:

5'-GGAAGAGCAGAGATATACGTXCCAGGTGGAGCACCCAGG-3'

(SEQ ID NO: 10)

and sequences complementary therewith wherein "X" represents a single base-pair polymorphism of G in a population unaffected with the HH gene mutation and A in a population affected with the HH gene mutation.

16. A genetic marker predictive of a hereditary hemochromatosis (HH) gene mutation comprising a partial sequence of the human genome including at least 16 contiguous nucleotide residues including "X" in the following nucleotide sequence:

5'- TATTTCCTTCCTCCAACCTATAGAAGGAAGTGAAAGTTCCAG

TCTTCCTGGCAAGGGTAAACAGATCCCCTCTCCTCATCCTTC

CTCTTTCCTGTCAAGTGCCTCCTTTGGTGAAGGTGACACATC

ATGTGACCTCTTCAGTGACCACTCTACGGTGTCGGGCCTTGA

ACTACTACCCCCAGAACATCACCATGAAGTGGCTGAAGGATA

AGCAGCCAATGGATGCCAAGGAGTTCGAACCTAAAGACGTA

TTGCCCAATGGGGATGGGACCTACCAGGGCTGGATAACCTTG

GCTGTACCCCCTGGGGAAGAGCAGAGATATACGTXCCAGGT

GGAGCACCCAGGCCTGGATCAGCCCCTCATTGTGATCTGGGG

TATGTGACTGATGAGAGCCAGGAGCTGAGAAAATCTATTGGG

GGTTGAGAGGAGTGCCTGAGGAGGTAATTATGGCAGTGAGA

TGAGGATCTGCTCTTTGTTAGGGGGTGGGCTGAGGGTGGCAA

TCAAAGGCTTTAACTT-3'

(SEQ ID NO: 13)

and sequences complementary therewith
wherein "X" represents a single base-pair polymorphism of G in a population unaffected with the HH gene mutation and A in a population affected with the HH gene mutation.

17. Complementary sequences of any one of the sequences of SEQ ID NO: 1 through SEQ ID NO: 13.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
       ( A ) LENGTH: 39 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

GGAAGAGCAG AGATATACGT GCCAGGTGGA GCACCCAGG                   3 9

( 2 ) INFORMATION FOR SEQ ID NO:2:

( i ) SEQUENCE CHARACTERISTICS:
       ( A ) LENGTH: 39 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

( 2 ) INFORMATION FOR SEQ ID NO:3:

( i ) SEQUENCE CHARACTERISTICS:
        ( A ) LENGTH: 517 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

```
GGAAGAGCAG AGATATACGT ACCAGGTGGA GCACCCAGG                          39

TATTTCCTTC CTCCAACCTA TAGAAGGAAG TGAAAGTTCC AGTCTTCCTG GCAAGGGTAA    60
ACAGATCCCC TCTCCTCATC CTTCCTCTTT CCTGTCAAGT GCCTCCTTTG GTGAAGGTGA   120
CACATCATGT GACCTCTTCA GTGACCACTC TACGGTGTCG GGCCTTGAAC TACTACCCC    180
AGAACATCAC CATGAAGTGG CTGAAGGATA AGCAGCCAAT GGATGCCAAG GAGTTCGAAC   240
CTAAAGACGT ATTGCCCAAT GGGGATGGGA CCTACCAGGG CTGGATAACC TTGGCTGTAC   300
CCCCTGGGGA AGAGCAGAGA TATACGTGCC AGGTGGAGCA CCCAGGCCTG GATCAGCCCC   360
TCATTGTGAT CTGGGGTATG TGACTGATGA GAGCCAGGAG CTGAGAAAAT CTATTGGGGG   420
TTGAGAGGAG TGCCTGAGGA GGTAATTATG GCAGTGAGAT GAGGATCTGC TCTTTGTTAG   480
GGGGTGGGCT GAGGGTGGCA ATCAAAGGCT TTAACTT                            517
```

( 2 ) INFORMATION FOR SEQ ID NO:4:

( i ) SEQUENCE CHARACTERISTICS:
        ( A ) LENGTH: 517 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

```
TATTTCCTTC CTCCAACCTA TAGAAGGAAG TGAAAGTTCC AGTCTTCCTG GCAAGGGTAA    60
ACAGATCCCC TCTCCTCATC CTTCCTCTTT CCTGTCAAGT GCCTCCTTTG GTGAAGGTGA   120
CACATCATGT GACCTCTTCA GTGACCACTC TACGGTGTCG GGCCTTGAAC TACTACCCC    180
AGAACATCAC CATGAAGTGG CTGAAGGATA AGCAGCCAAT GGATGCCAAG GAGTTCGAAC   240
CTAAAGACGT ATTGCCCAAT GGGGATGGGA CCTACCAGGG CTGGATAACC TTGGCTGTAC   300
CCCCTGGGGA AGAGCAGAGA TATACGTACC AGGTGGAGCA CCCAGGCCTG GATCAGCCCC   360
TCATTGTGAT CTGGGGTATG TGACTGATGA GAGCCAGGAG CTGAGAAAAT CTATTGGGGG   420
TTGAGAGGAG TGCCTGAGGA GGTAATTATG GCAGTGAGAT GAGGATCTGC TCTTTGTTAG   480
GGGGTGGGCT GAGGGTGGCA ATCAAAGGCT TTAACTT                            517
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:5:

TGGCAAGGGT AAACAGATCC                                         20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:6:

CTCAGGCACT CCTCTCAACC                                         20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:7:

GGAAGAGCAG AGATATACGT G                                       21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (x i) SEQUENCE DESCRIPTION: SEQ ID NO:8:

GGAAGAGCAG AGATATACGT A                                       21

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO ( x i ) SEQUENCE DESCRIPTION: SEQ ID NO:9:

CCAGGTGGAG CACCCAGG                                                                18

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

GGAAGAGCAG AGATATACGT NCCAGGTGGA GCACCCAGG                                         39

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

CTGAAAGGGT GGGATCACAT                                                              20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

CAAGGAGTTC GTCAGGCAAT                                                              20

( 2 ) INFORMATION FOR SEQ ID NO:13:

( i ) SEQUENCE CHARACTERISTICS:
        ( A ) LENGTH: 517 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

TATTTCCTTC CTCCAACCTA TAGAAGGAAG TGAAAGTTCC AGTCTTCCTG GCAAGGGTAA                   60

| | | | | | | |
|---|---|---|---|---|---|---|
| ACAGATCCCC | TCTCCTCATC | CTTCCTCTTT | CCTGTCAAGT | GCCTCCTTTG | GTGAAGGTGA | 120 |
| CACATCATGT | GACCTCTTCA | GTGACCACTC | TACGGTGTCG | GGCCTTGAAC | TACTACCCC | 180 |
| AGAACATCAC | CATGAAGTGG | CTGAAGGATA | AGCAGCCAAT | GGATGCCAAG | GAGTTCGAAC | 240 |
| CTAAAGACGT | ATTGCCCAAT | GGGGATGGGA | CCTACCAGGG | CTGGATAACC | TTGGCTGTAC | 300 |
| CCCCTGGGGA | AGAGCAGAGA | TATACGTNCC | AGGTGGAGCA | CCCAGGCCTG | GATCAGCCCC | 360 |
| TCATTGTGAT | CTGGGGTATG | TGACTGATGA | GAGCCAGGAG | CTGAGAAAAT | CTATTGGGGG | 420 |
| TTGAGAGGAG | TGCCTGAGGA | GGTAATTATG | GCAGTGAGAT | GAGGATCTGC | TCTTTGTTAG | 480 |
| GGGGTGGGCT | GAGGGTGGCA | ATCAAAGGCT | TTAACTT | | | 517 |